United States Patent [19]

Erpenbach et al.

[11] 4,352,761

[45] Oct. 5, 1982

[54] PRODUCTION OF ACETYL CHLORIDE

[75] Inventors: Heinz Erpenbach, Cologne; Klaus Gehrmann; Winfried Lork, both of Erftstadt; Peter Pring, Hürth, all of Fed. Rep. of Germany

[73] Assignee: Hoechst Aktiengesellschaft, Fed. Rep. of Germany

[21] Appl. No.: 256,387

[22] Filed: Apr. 22, 1981

[30] Foreign Application Priority Data

May 2, 1980 [DE] Fed. Rep. of Germany ....... 3016900

[51] Int. Cl.$^3$ ............................................. C07C 51/58
[52] U.S. Cl. ................................................. 260/544 A
[58] Field of Search ..................................... 260/544 A

[56] References Cited

U.S. PATENT DOCUMENTS 1,911,589  5/1933  Steinhauser .................... 260/544 A
3,632,643  1/1972  Prichard ......................... 260/544 A
3,845,121 10/1974  Eubanks et al. ................ 260/544 A Primary Examiner—Natalie Trousof
Assistant Examiner—L. Hendriksen
Attorney, Agent, or Firm—Connolly and Hutz

[57] ABSTRACT

The invention relates to a process for making acetyl chloride by reacting methoxy chloride with carbon monoxide under practically anhydrous conditions, at temperatures of 350° to 575° K, under pressures of 1 to 300 bars, and in the presence of a catalyst system containing at least one of the noble metals selected from rhodium, palladium, iridium or their compounds, iodine and/or its compounds and optionally trialkylphosphine oxide or triarylphosphine oxide, as well as an inert organic solvent. The invention provides more specifically for the reaction to be effected in the presence of a catalyst system containing n-heptane as the inert solvent and as additional ingredients methyltrialkyl phosphonium iodide and/or methyltriarylphosphonium iodide and at least one compound of chromium, molybdenum or tungsten.

5 Claims, 1 Drawing Figure

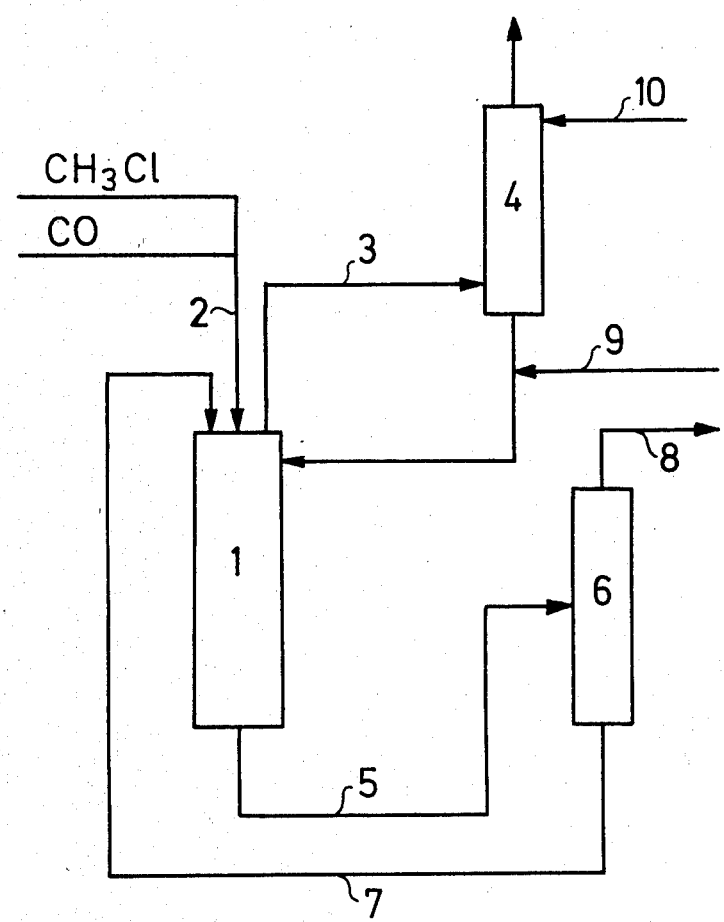

PRODUCTION OF ACETYL CHLORIDE

The present invention relates to a process for making acetyl chloride by reacting methyl chloride with carbon monoxide under practically anhydrous conditions, at temperatures of 350 to 575 K., under pressures of 1 to 300 bars, and in the presence of a catalyst system containing at least one of the noble metals selected from rhodium, palladium, iridium or their compounds, iodine and/or its compounds and optionally trialkylphosphine oxide or triarylphosphine oxide, as well as an inert organic solvent, which comprises: effecting the reaction in the presence of a catalyst system containing n-heptane as the inert solvent and as additional ingredients methyltrialkyl phosphonium iodide and/or methyltriaryl phosphonium iodide and at least one compound of chromium, molybdenum or tungsten.

Processes for making acetyl halides from alkyl halides and carbon monoxide in the presence of a catalyst system containing compounds of rhodium or iridium, an iodide, a tertiary phosphine and/or tertiary phosphine oxide, e.g. triphenylphosphine oxide, in an inert solvent, e.g. toluene, hexane, octane, cyclohexane etc have already been described (cf. Japanese publish Specifications Nos. 53/46912 (1978); 53/63307 (1978); and 53/63308 (1978)). As further ingredients, the catalyst system just described may contain one or more phosphonates of the formula $(R)_2P(=O)OR$, phosphoric acid esters of the formula $(RO_3)PO$ or phosphoric acid triamides of the formula $(R_2N)_3PO$. The product obtained by this reaction is a one-phase mixture having solid catalyst proportions contained therein. To isolate desirable acetyl halide, e.g. acetyl chloride, and to recover or recycle catalyst proportions including solvent and unreacted alkyl halide, e.g. methyl chloride, it is obligatory for the reaction mixture to be subjected to distillative work-up.

The precipitation during that operation of further catalyst proportions, for which it is equally necessary to be recycled, entails considerable technical difficulties. The change in concentration which occurs during the distillative work-up causes salt-like catalyst to be deposited to an increasing extent inside tubings, columns and evaporators. This invariably results in the production becoming disorganized and in loss of expensive catalyst. In addition to this, as a result of the thermal stress the catalyst is exposed to inside the distilling apparatus, the catalytic activity is readily impaired so that it is necessary for the catalyst to be continually renewed.

The process of this invention has now been found to avoid these technically adverse effects. More particularly, it has been found that the use of a catalyst system comprised of noble metal compounds belonging to subgroup 8 of the periodic system of the elements, iodine (-compounds) and optionally trialkyl- and/or triarylphosphine oxide in admixture with compounds of at least one metal belonging to subgroup 6 of the periodic system of the elements, and in further admixture with methyltrialkylphosphonium iodide and/or methyltriarylphosphonium iodide and n-heptane, in the reaction of methyl chloride and CO under increased pressure, if desired, and at elevated temperature effects the separation of the resulting reaction product into two phases. In connection with this, the entire catalyst system has unexpectedly been found to undergo complete dissolution and form the denser lower phase, whilst the bulk portion of acetyl chloride formed is contained in the upper solvent phase. As compared with the prior art methods, the phase separation in accordance with this invention of catalyst system and acetyl chloride/solvent offers considerable technically beneficial effects.

1. By subjecting the reaction product to phase separation, it is freed from catalyst which is recycled to the reactor. In other words, it is no longer necessary for solid catalyst to be recovered by distillative treatment which invariably results in portions of catalyst being lost.

2. The catalyst is retained in the reaction system and does not go forward into the distillative work-up stage so that catalyst is not liable to precipitate in distilling apparatus or to get lost.

3. Thermal stress and premature loss of catalytic activity as normally encountered during the work-up of the catalyst are not liable to occur.

4. The present process is technically easier to carry out and it proceeds at higher velocity upon the addition of compounds of chromium, molybdenum or tungsten.

The noble metals selected from rhodium, palladium, iridium and the metals selected from chromium, molybdenum and tungsten should preferably be used in the form of their chlorides (e.g. $RhCl_3.3H_2O$; $CrCl_3.6H_2O$), acetates, carbonyls or as complex compounds, e.g. $Rh(CO)Cl[P(C_6H_5)_3]_2$, $Ir(CO)Cl[P(C_6H_5)_3]_2$, $RhCl[P(C_6H_5)_3]_3$, $[Rh(CO)_2Cl]_2$, $HIr(CO)[P(C_6H_5)_3]_3$, $HRh(CO)[P(C_6H_5)_3]_3$.

Methyl iodide is the iodine compound which is most preferably used, but ethyl iodide and hydrogen iodide can also be employed.

In the general terms trialkylphosphine oxide and methyltrialkylphosphonium iodide, the word "alkyl" preferably stands for methyl, ethyl, propyl and butyl, and in the general terms triarylphosphine oxide and methyltriarylphosphonium iodide, the word "aryl" preferably stands for phenyl.

The catalyst system comprised of noble metal(-compound)/compound of chromium, molybdenum or tungsten/iodine(-compound)/tertiary phosphine oxide/quaternary phosphonium iodide/n-heptane should preferably be used in a molar ratio of 1:(1–8):(1–100):(0–50):(1–100):(50–500).

It is also preferable to use 0.0001 up to 0.01 mol of noble metal(-compound) and 0.0001 up to 0.08 mol of compound(s) of chromium, molybdenum or tungsten.

The reaction in accordance with this invention should preferably be effected under a pressure of 20 to 180 bars and at a temperature of 150° to 250° C. (423–523 K.).

The invention will now be described with reference to the accompanying diagrammatic representation showing a typical form of flow scheme for carrying out the present process.

Methyl chloride and carbon monoxide coming from a conduit (2) are reacted under a preferred pressure of 20 to 180 bars and at a preferred temperature of 150° to 250° C. (423–523 K.) to give acetyl chloride, the reaction being effected in an autoclave (1) provided with a mixing means in the presence of a catalyst system comprised of noble metals selected from rhodium, palladium or iridium or their compounds, chromium, molybdenum or tungsten or their compounds, iodine and/or its compounds, preferably methyl iodide, and methyltrialkylphosphonium iodide and/or methyltriarylphosphonium iodide, preferably methyltriphenylphosphonium iodide, and optionally trialkyl phosphine oxide or triarylphosphine oxide, preferably triphenylphosphine oxide. A small proportion of gaseous by-products, such as methane or impurities originating from the carbon monoxide, such as argon or nitrogen, was removed together with unreacted carbon monoxide through conduit (3) and a scrubbing stage (4). Fresh methyl chloride and carbon monoxide replacing consumed material, were supplied through conduit (2). The reaction product together with catalyst was introduced through a conduit (5) into a separator (6), in which the reaction product was separated into a catalyst phase (lower phase), and product phase (upper phase). A quantity of catalyst phase with the entire catalyst therein, corresponding to that introduced into the separator was recycled through conduit (7) to the reactor (1), whilst formed acetyl chloride together with unreacted methyl chloride, proportions of methyl iodide and n-heptane was removed through conduit (8) and separated by distillation as usual. Unreacted starting materials and solvent were recycled into the system, through conduits (9) and (10).

Example 1

1.95 g $RhCl_3.3H_2O$, 7.91 g $CrCl_3.6H_2O$, 3.4 g triphenylphosphine oxide, 30 g methyl-triphenylphosphonium iodide, 15.8 g methyl iodide, 150.5 g methyl chloride and 150.5 g n-heptane were placed in an autoclave of corrosionproof stainless steel and maintained under a constant CO-pressure of 75 bars therein. After a reaction period of 1 hour at 453 K., the reaction product was taken from the autoclave and placed in a separating funnel. The reaction product consisted of two phases free from solid matter. The two phases were distilled separately from one another. After this had been done, the lower layer was found to contain the entire salt-like constituents of the catalyst used; the upper layer distilled over practically free from residue. 110 g acetyl chloride (47% of the theoretical) was obtained. This corresponded to a space/time-yield of 275 g $CH_3COCl/l$ reaction volume per hour or to 145 g $CH_3COCl/g$ Rh per hour.

Example 2

1.95 g $RhCl_3.3H_2O$, 3.96 g $CrCl_3.6H_2O$, 2.55 g methy-tri-n-butylphosphonium iodide, 27.0 g methyltriphenylphosphonium iodide, 3.4 g triphenylphosphine oxide, 15.8 g methyl iodide, 150.5 g methyl chloride and 150.5 g n-heptane were weighed into an autoclave of corrosionproof stainless steel and a CO-pressure of 75 bars was established therein. After a reaction period of 1 hour at 453 K. inside the autoclave, a two-phase reaction product was obtained. Once again the salt-like catalyst constituents were contained in the lower layer, whilst the upper layer distilled over practically free from residue. 119 g (51% of the theoretical) acetyl chloride was obtained. This corresponded to a space/time-yield of 298 g $CH_3COCl/l$ reaction volume per hour or to 157 g $CH_3COCl/g$ Rh per hour.

Example 3

1.95 g $RhCl_3.3H_2O$, 15.8 g $CrCl_3.6H_2O$, 3.4 g triphenylphosphine oxide, 120 g methyl-triphenylphosphonium iodide, 15.8 g methyl iodide, 150.5 g methyl chloride and 150.5 g n-heptane were placed in an autoclave of corrosionproof stainless steel, and reacted therein under a CO-pressure of 75 bars at a temperature of 453 K. After a reaction period of 0.8 hour, a two-phase reaction product was taken from the autoclave. Once again the lower layer was found to contain the catalyst. 122 g acetyl chloride (52% of the theoretical) was obtained. This corresponded to a space/time-yield of 381 g $CH_3COCl/l$ reaction volume per hour or to 161 g $CH_3COCl/g$ Rh per hour.

Example 4

0.98 g $RhCl_3.3H_2O$, 3.96 g $CrCl_3.6H_2O$, 30 g methyl-triphenylphosphonium iodide, 15.8 g methyl iodide, 150.5 g methyl chloride and 150.5 g n-heptane were weighed into an autoclave of corrosionproof stainless steel, a CO-pressure of 75 bars was established therein and the whole was reacted over a period of 1 hour at 453 K. The reaction product was found to contain 101 g acetyl chloride (43% of the theoretical); corresponding to a space/time-yield of 252 g $CH_3COCl/l$ reaction volume per hour or to 266 g $CH_3COCl/g$ Rh per hour.

Example 5

1.95 g $RhCl_3.3H_2O$, 7.91 g $CrCl_3.6H_2O$, 3.4 g triphenylphosphine oxide, 60 g methyl-triphenylphosphonium iodide, 15.8 g methyl iodide, 150.5 g methyl chloride and 150.5 g n-heptane were placed in an autoclave of corrosionproof stainless steel and a CO-pressure of 75 bars was established therein. After a reaction period of 1 hour at 453 K., a two-phase reaction product free from solid matter was obtained. It was analyzed and found to contain 126 g acetyl chloride (54% of the theoretical), corresponding to a space/time-yield of 315 g $CH_3COCl/l$ reaction volume per hour or to 166 g $CH_3COCl/g$ Rh per hour.

Example 6

1.95 g $RhCl_3.3H_2O$, 7.91 g $CrCl_3.6H_2O$, 3.4 g triphenylphosphine oxide, 30 g methyl-triphenylphosphonium iodide, 15.8 g methyl iodide, 150.5 g methyl chloride and 150.5 g n-heptane were placed in an autoclave of corrosionproof stainless steel and a CO-pressure of 75 bars was established therein. After a reaction period of 1 hour at 453 K., a two-phase reaction product free from solid matter was obtained. The lower layer was recycled to the autoclave, admixed once again with the above specified proportions of methyl iodide, n-heptane and methyl chloride, and a CO-pressure of 75 bars was established once again. After a reaction period of 1 hour at 453 K., a two-phase reaction product was taken again from the autoclave. The first re-use of the catalyst just described was repeated another three times.

After the catalyst had been recycled altogether four times, the experiment was terminated. 505 g acetyl chloride (43% of the theoretical) was obtained during an total reaction time of 5 hours. The space/time-yield was 253 g $CH_3COCl/l$ reaction volume per hour and the catalyst activity was 133 g $CH_3COCl/g$ Rh per hour.

Example 7

1.95 g $RhCl_3.3H_2O$, 7.91 g $CrCl_3.6H_2O$, 3.4 g triphenylphospine oxide, 120 g methyl-triphenylphosphonium iodide, 15.8 g methyl iodide, 150.5 g methyl chloride and 150.5 g n-heptane were placed in an autoclave of corrosionproof stainless steel and reacted therein at 453 K. under a CO-pressure of 75 bars. After a reaction period of 0.6 hour, a two-phase mixture was taken from the autoclave. The lower layer was found to contain the catalyst. 115 g acetyl chloride (49% of the theoretical) was obtained, corresponding to a space/time-yield of 479 g $CH_3COCl/l$ reaction volume per hour or to 252 g $CH_3COCl/l$ Rh per hour.

Example 8 (Comparative Example)

1.95 g RhCl$_3$.3H$_2$O, 3.4 g triphenylphosphine oxide, 77.9 g triphenylphosphine, 15.8 g methyl iodide, 150.5 g methyl chloride and 150 g n-octane were placed in an autoclave of corrosionproof stainless steel and a CO-pressure of 75 bars was established therein. After a reaction period of 1 hour at 453 K., the reaction product was taken from the autoclave. It was found to contain a good deal of the catalyst mixture in the form of smeary to crystalline precipitated material. After separation of solid residue, distillation of the remaining liquid phase and analysis, 39 g acetyl chloride (16.7% of the theoretical) was obtained. This corresponded to a space/time-yield of 98 g CH$_3$COCl/l reaction volume per hour or to 51 g CH$_3$COCl/g Rh per hour.

Example 9

An autoclave of stainless steel was filled with 1.5 l reaction mixture. It contained 18 millimols Rh/l, which was used in the form of RhCl$_3$.3H$_2$O. The molar ratio of rhodium compound:chromium compound:methyl iodide:triphenylphosphine oxide:methyltriphenylphosphonium iodide:n-heptane was 1:4:15:1.65:20:202. The reactor was supplied per hour with 264 g fresh methyl chloride. The reaction pressure was maintained at 75 bars by the continuous introduction of CO and the reaction temperature was 450 to 455 K. The reaction product taken from the reactor at the same rate as starting material was introduced thereinto was introduced into a separator and separated into two phases therein. The lower layer which was recycled to the reactor contained the catalyst solution. The upper product phase coming from the separator contained n-heptane together with about 37 weight % acetyl chloride, about 6 weight % methyl chloride and about 10 weight % methyl iodide, and it was worked up as usual. 390 g/h acetyl chloride was obtained. Unreacted methyl chloride, methyl iodide and n-heptane were recycled to the reactor. Based on the methyl chloride used, acetyl chloride was obtained in a yield of 95%. This corresponded to a space/time-yield of 260 g CH$_3$COCL/l reaction volume per hour or to a catalytic efficiency of 140 g CH$_3$COCl/g Rh per hour.

We claim:

1. In a process for making acetyl chloride by reacting methyl chloride with carbon monoxide under practically anhydrous conditions, at temperatures of 350 to 575 K., under pressures of 1 to 300 bars, and in the presence of a catalyst system containing at least one of the noble metals selected from rhodium, palladium, iridium or at least one compound thereof selected from the group consisting of a chloride, acetate, carbonyl, or complex compound; iodine or iodine compounds or mixtures of iodine and iodine compounds; and an inert organic solvent, the improvement which comprises: effecting the reaction in the presence of a catalyst system containing n-heptane as the inert solvent and as additional ingredients methyltrialkyl phosphonium iodide or methyltriaryl phosphonium iodide or mixtures thereof and at least one compound of chromium, molybdenum or tungsten selected from the group consisting of a chloride, acetate, carbonyl, or complex compound, thereby effecting the separation of the resulting reaction product into two phases, the entire catalyst system undergoing complete dissolution and forming the denser lower phase, whilst the bulk portion of acetyl chloride formed is contained in the upper solvent phase.

2. A process as claimed in claim 1, wherein methyl iodide, ethyl iodide or hydrogen iodide is used as the iodine compound.

3. A process as claimed in claim 1, wherein the reaction is carried out in the presence of trialkyl-phosphine oxide or triarylphosphine oxide.

4. A process as claimed in claim 3, wherein the alkyl moiety of the trialkylphosphine oxide and the methyltrialkyl phosphonium iodide is selected from the group consisting of methyl, ethyl, propyl and butyl, and aryl moiety of the triarylphosphine oxide and the methyltriaryl phosphonium iodide is phenyl.

5. A process as claimed in claim 1, wherein the catalyst system comprised of noble metal(-compound)-/compound of chromium, molybdenum or tungsten/iodine(-compound)/tertiary phosphine oxide/quaternary phosphonium iodide/n-heptane is used in a molar ratio of 1:(1–8):(1–100):(0–50):(1–100):(50–500).

* * * * *